US00PP15473P2

(12) United States Plant Patent
Olesen et al.

(10) Patent No.: US PP15,473 P2
(45) Date of Patent: Jan. 11, 2005

(54) MINATURE ROSE PLANT NAMED 'POULHI015'

(50) Latin Name: *Rosa hybrida*
Varietal Denomination: POULhi015

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/813,540

(22) Filed: Mar. 29, 2004

(51) Int. Cl.[7] ..... A01H 5/00
(52) U.S. Cl. ..... Plt./107
(58) Field of Search ..... Plt./107

*Primary Examiner*—Anne Marie Grunberg
*Assistant Examiner*—Annette H Para

(57) ABSTRACT

A new miniature rose plant which has abundant, pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULhi015'.

SUMMARY OF THE INVENTION

The present invention constitutes a new and distinct variety of miniature rose plant which originated from a controlled crossing between the female parent, an un-named seedling, and the male parent, an un-named seedling. The two parents were crossed in 1993. The resulting seeds were planted in a controlled environment. The new variety is named 'POULhi015'.

The new *rose* may be distinguished from its seed parent by the following combination of characteristics:

1. The female seed parent has amber yellow flower color, while 'POULhi015' has a pink flower color.
2. The female seed parent has a taller growth habit than that of 'POULhi015'.

The new variety may be distinguished from its pollen parent, an un-named seedling, by the following combination of characteristics:

1. The pollen parent has yellow flowers while 'POULhi015' has pink flowers.
2. The pollen parent has a taller growth habit than that of 'POULhi015'.

The objective of the hybridization of this *rose* variety for commercial culture was to create a new and distinct variety with unique qualities, such as:

1. Uniform and abundant pink flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventors, and distinguish 'POULhi015' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULhi015' was selected by the inventors as a single plant from the progeny of the hybridization in 1993.

Asexual reproduction of 'POULhi015' by cuttings and traditional budding was first done by L. Pernille and Mogens N. Olesen in their nursery in Fredensborg, Denmark in 1994. This initial and other subsequent propagations conducted in controlled environments have demonstrated that the characteristics of 'POULhi015' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULhi015'. Specifically illustrated in the drawing:

FIG. 1.1; Open flower, and stem showing open flower and the attachment of leaves, peduncle;

FIG. 1.2; Flower bud partially opened;

FIG. 1.3; Flower petals, detached;

FIG. 1.4; Sepals, receptacle, and pedicel;

FIG. 1.5; Juvenile growth;

FIG. 1.6; Mature leaves;

FIG. 1.7; Bare stems exhibiting thorns.

DETAILED DESCRIPTION OF THE VARIETY

The following is a description of 'POULhi015', as observed in its growth in a field nursery in Jackson County, Oreg. Observed plants are 3 months of age and were grown on *Rosa multiflora* understock. Color references are made using The Royal Horticultural Society (London, England) Colour Chart, 1995, except where common terms of color are used.

For a comparison, several physical characteristics of the rose variety 'POULlute', a rose variety from the same inventors described and illustrated in U.S. Plant Pat. No. 10,727 issued Apr. 30, 1977, are compared to 'POULhi015' in Chart 1.

CHART 1

| Characteristic | 'POULhi015' | 'POULlute' |
|---|---|---|
| General tonality of open flower | Red Group 38A with light intonations of Red Group 52C | Red Group 36A |
| Petalage | 35 petals | 30 to 35 petals |
| Coloration of filaments | Yellow Group 12A | Green-Yellow Group 1B |
| Open flower diameter | 45 mm | 40 to 50 mm |

FLOWER AND FLOWER BUD

Blooming habit: Continuous.

Flower bud:

*Size.*—Upon opening, 25 mm in length from base of receptacle to end of bud. Bud diameter is 12 to 15 mm.

*Bud form.*—Pointed ovoid.

*Bud color.*—As sepals unfold, Red Group 51C; Red Group 51C to 51D at ¼ opening.

*Sepals.*—Upper Surface: Color: Yellow-Green Group 146A. Surface: Light pubescence. Lower Surface: Color: Yellow-Green Group 146B. Texture: Smooth with stipitate glands. Shape: Sepal apex is cirrhose. Base is flat at union with receptacle. Margins: Margins have strong foliaceous appendages on three of the five sepals. Stipitate glands present in medium quantity. Size: 24 m (l)×8 mm (w).

*Receptacle.*—Surface: Slightly pubescent. Shape: Funnel shaped. Size: 5 mm (h)×6 mm (w). Color: Yellow-Green Group 144B.

*Peduncle.*—Surface: Smooth and slightly pubescent. Length: 25 to 30 mm. Color: Yellow-Green Group 144B. Strength: Strong.

*Borne.*—In small clusters, 1 to 3 flower buds per stem on average.

Flower bloom:

*Fragrance.*—Light rose scent.

*Duration.*—The blooms have a duration on the plant of approximately 10 to 14 days. Petals fall cleanly away from plant after flowers have fully matured.

*Size.*—Average flower diameter is 45 mm when open. Flower depth is 18 mm.

*Form.*—General shape is cupped with a tight center. Shape of flower when viewed from the side: Upon opening, upper part: Flat. Upon opening, lower part-:Flattened convex. Open flower, upper part: Flat. Open flower, lower part: Concave.

*Petalage.*—30 petals under normal conditions with 4 petaloids.

Color:

*Upon opening, petals.*—Outermost petals: Outside Side: Red Group 51C with intonations of Red Group 54B at basal zone. Inner Side: Red Group 49C with intonations of Orange Group 25C at basal zone. Innermost petals: Outer Side: Red Group 51C with intonations of Red Group 54B at basal zone. Inner Side: Red Group 49C with intonations of Orange Group 25C at basal zone.

*Upon opening, basal petal spots.*—Outermost petals: Outer Side: Yellow Group 12B. Inner Side: Yellow Group 12A. Innermost petals: Outer Side: Yellow Group 12B. Inner Side: Yellow Group 12A.

*After opening, petals.*—Outermost petals: Outer Side: Red Group 48D with intonations of Red Group 47D. Inner Side: Red Group 56B. Innermost petals: Outer Side: Red Group 38A. Inner Side: Red Group 36A.

*After opening, basal petal spots.*—Outermost petals: Outside Side: Yellow Group 12C. Inner Side: Yellow Group 12B. Innermost petals: Outer Side: Yellow Group 12B to 12C. Inner Side: Yellow Group 12B.

General tonality: On open flower Red Group 38A with very light intonations of Red Group 52C. No change in the general tonality at the end of the $7^{th}$ day. Afterwards, general tonality is Red Group 52D.

Petals:

*Petal reflex.*—Slightly.

*Petal margin.*—Entire with point in center of margin.

*Shape.*—Generally obovate. Apex: Rounded. Base: Acute.

*Size.*—20 mm (l)×10 mm (w).

*Thickness.*—Thin.

*Arrangement.*—Not formal.

Petaloids:

*Quantity.*—3 to 5.

*Size.*—21 mm (l)×10 mm (w).

*Shape.*—Base is acute. Apex is round.

*Color.*—Upper Surface: Red Group 38B. Lower Surface: Red Group 38C.

Reproductive organs:

*Pistils.*—Length: 5 mm. Quantity: 41 (actual count).

*Pollen.*—None observed.

*Anthers.*—Size: 2 mm. Color: Yellow Group 12A. Quantity: 56 (actual count).

*Filaments.*—Color: Yellow Group 12A. Length: 5 to 6 mm.

*Stigmas.*—Level with the height of the anthers. Color: Greyed-Yellow Group 160D.

*Styles.*—Color: Greyed-Yellow Group 160D.

*Seed formation.*—Not observed.

PLANT

Plant growth: Compact and bushy. When grown as a pot plant, the average height of the plant itself is 30 to 35 cm and the average width is 35 cm.

Stems:

*Color.*—Young wood: Yellow-Green Group 144B. Older wood: Yellow-Green Group 144B.

*Surface.*—Young wood: Smooth. Older wood: Smooth.

Thorns:

*Incidence.*—8 mm per 10 cm of stem.

*Size.*—6 mm.

*Color.*—Greyed-Red Group 181A.

*Shape.*—Deeply concave.

Plant foliage: Normal number of leaflets on normal leaves in middle of the stem: 5 leaflets.

*Compound leaf size.*—80 mm (l)×45 mm (w).

*Color.*—Juvenile foliage: Upper Leaf Surface: Yellow Green Group 146A. Lower Leaf Surface: Yellow Green Group 148A. Mature foliage: Upper Leaf Surface: Yellow-Green Group 146A. Lower Leaf Surface: Yellow-Green Group 147B. Anthocyanin intonation: Location: Leaf margins and rachis of juvenile foliage. Color: Greyed-Red Group 184A.

Plant leaves and leaflets:

*Stipules.*—Size: 20 mm in length. Shape: Linear with outward extending apecies. Quantity: 2 per compound leaf. Margins: Finely serrated with stipitate glands. Color: Yellow-Green Group 144A.

*Petiole.*—Length: 25 mm. Color: Yellow-Green Group 144B. Underneath: Thorns and stipitate glands observed.

*Rachis.*—Size: 35 mm. Color: Yellow-Green Group 144B. Underneath: Thorns and stipitate glands observed.

*Leaflet.*—Size: 28 mm (l)×18 mm(w). Edge: Finely serrated. Shape: Generally ovate. Cuspidate leaf apex. Leaf base is rounded. Texture: Smooth. Arrangement: Odd pinnate. Venation: Reticulate. Glossiness: Glossy. Thickness: Thick.

Disease resistance: Above average resistance to mildew, black spot, and Botrytis under normal growing conditions in Jackson County, Oreg.

Cold hardiness: 'POULhi015' has been found to be cold tolerant to USDA cold hardiness zone 6.

It is claimed:

1. A new and distinct variety of rose plant of the miniature class named 'POULhi015', substantially as herein illustrated and described as a distinct and novel rose variety due to its abundant, pink flowers, vigorous growth, compact habit, suitability for production from softwood cuttings in pots, and durable flowers and foliage which make the variety suitable for distribution in the floral industry.

* * * * *

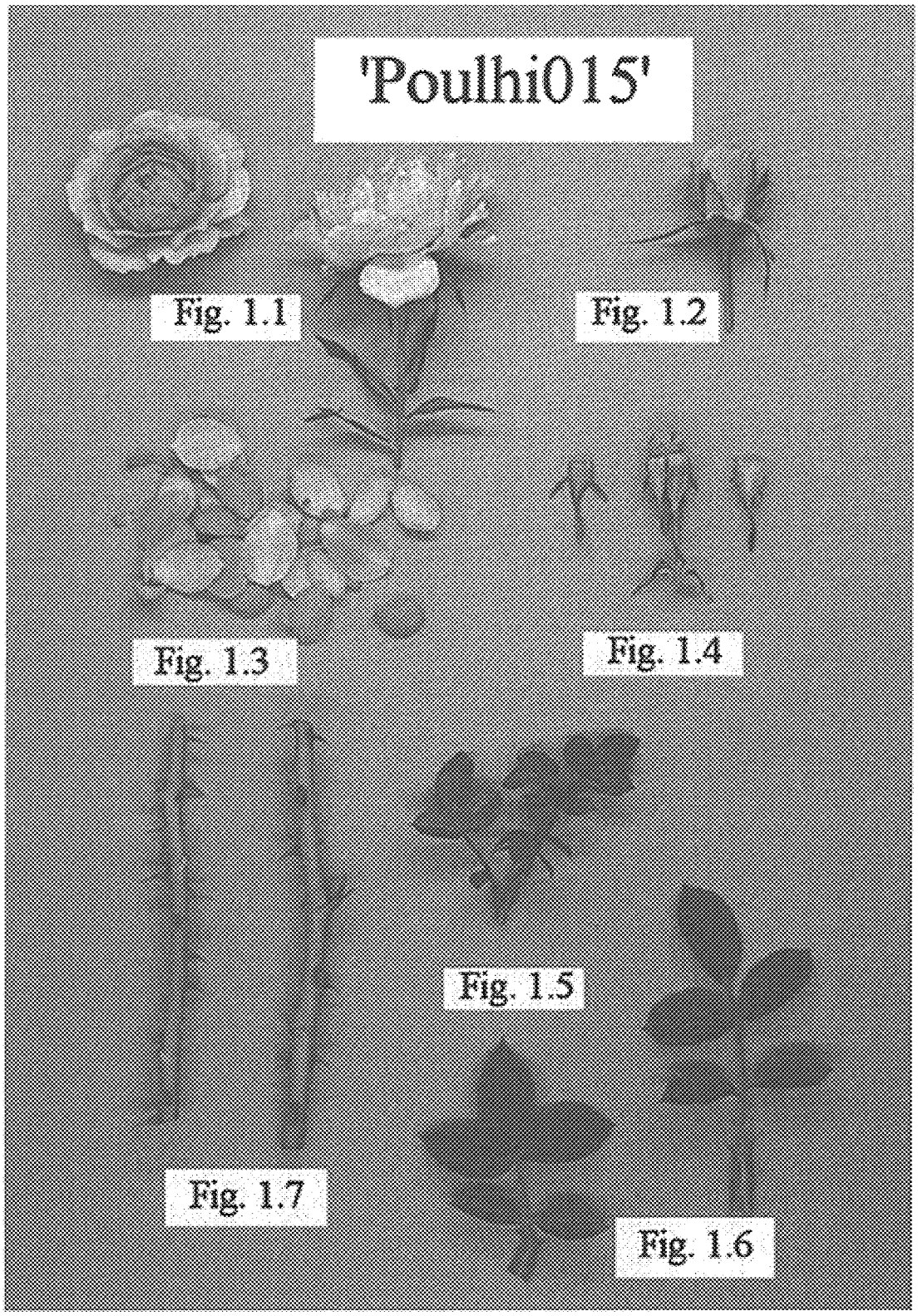
'Poulhi015'
Fig. 1.1
Fig. 1.2
Fig. 1.3
Fig. 1.4
Fig. 1.5
Fig. 1.7
Fig. 1.6